(12) United States Patent
Iijima et al.

(10) Patent No.: US 8,449,627 B2
(45) Date of Patent: *May 28, 2013

(54) TWO-PART HAIR DYE

(75) Inventors: Makoto Iijima, Sumida-ku (JP);
Naohiro Ando, Sumida-ku (JP); Takashi Matsuo, Sumida-ku (JP); Yuko Nobuto, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/572,140

(22) Filed: Aug. 10, 2012

(65) Prior Publication Data
US 2012/0305021 A1 Dec. 6, 2012

Related U.S. Application Data

(63) Continuation of application No. 13/146,157, filed as application No. PCT/JP2010/001627 on Mar. 9, 2010, now Pat. No. 8,349,022.

(30) Foreign Application Priority Data

Mar. 11, 2009 (JP) .................................. 2009-058763
Dec. 10, 2009 (JP) .................................. 2009-280282

(51) Int. Cl.
*A61Q 5/10* (2006.01)

(52) U.S. Cl.
USPC ............................ 8/405; 8/552; 8/554; 8/555

(58) Field of Classification Search
USPC ..................................... 8/405, 552, 554, 555
See application file for complete search history.

(56) References Cited

U.S. PATENT DOCUMENTS

| | | | |
|---|---|---|---|
| 3,341,418 A | 9/1967 | Moses et al. | |
| 3,709,437 A | 1/1973 | Wright | |
| 4,823,985 A | 4/1989 | Grollier et al. | |
| 4,961,925 A | 10/1990 | Tsujino et al. | |
| 5,143,518 A | 9/1992 | Madrange et al. | |
| 5,848,730 A | 12/1998 | Kawase et al. | |
| 5,968,486 A | 10/1999 | Newell et al. | |
| 6,692,539 B2 | 2/2004 | Desenne et al. | |
| 7,938,864 B2 | 5/2011 | Miyabe et al. | |
| 7,955,400 B2 | 6/2011 | Fujinuma et al. | |
| 7,972,389 B2 | 7/2011 | Matsunaga et al. | |
| 8,002,848 B2 | 8/2011 | Miyabe | |
| 8,021,439 B2 | 9/2011 | Miyabe et al. | |
| 8,025,702 B2 | 9/2011 | Fujinuma et al. | |
| 8,025,703 B2 | 9/2011 | Ogawa et al. | |
| 8,152,858 B2 | 4/2012 | Fujinuma et al. | |
| 8,153,108 B2 | 4/2012 | Fujinuma et al. | |
| 8,158,112 B2 | 4/2012 | Fujinuma et al. | |
| 2004/0213752 A1 | 10/2004 | Fujinuma et al. | |
| 2010/0126522 A1 | 5/2010 | Fujinuma et al. | |
| 2010/0126523 A1 | 5/2010 | Fujinuma et al. | |
| 2010/0236570 A1 | 9/2010 | Fujinuma et al. | |
| 2010/0242187 A1 | 9/2010 | Miyabe | |
| 2010/0251488 A1 | 10/2010 | Fujinuma et al. | |
| 2010/0257677 A1* | 10/2010 | Miyabe et al. | ..................... 8/405 |
| 2010/0299848 A1 | 12/2010 | Fujinuma et al. | |
| 2010/0313905 A1 | 12/2010 | Fujinuma et al. | |
| 2010/0316583 A1 | 12/2010 | Fujinuma et al. | |
| 2011/0073128 A1 | 3/2011 | Ogawa et al. | |
| 2011/0214682 A1 | 9/2011 | Fujinuma et al. | |
| 2011/0277782 A1 | 11/2011 | Iijima et al. | |
| 2012/0111974 A1 | 5/2012 | Fujinuma et al. | |

FOREIGN PATENT DOCUMENTS

| | | |
|---|---|---|
| DE | 1801518 | 1/1971 |
| EP | 113418 | 7/1984 |
| EP | 0 503 507 | 9/1992 |
| EP | 1 055 425 | 11/2000 |
| EP | 0 877 653 | 10/2002 |
| EP | 1291006 | 12/2003 |
| EP | 1 470 812 A1 | 10/2004 |
| GB | 1125528 | 8/1968 |
| GB | 2 254 341 | 10/1992 |
| GB | 2 293 157 | 3/1996 |
| JP | 48-68750 | 9/1973 |
| JP | S49-050144 | 5/1974 |
| JP | 55-49308 | 4/1980 |
| JP | 58-30282 | 6/1983 |
| JP | 59-108710 | 6/1984 |
| JP | 61-143412 | 7/1986 |
| JP | 62-242609 | 1/1987 |

(Continued)

OTHER PUBLICATIONS

Submission of Publications and the like, dated Nov. 10, 2008, in Japanese Patent Application No. 2004-130373.
Corresponding application filed in Japanese Application No. 2004-130373, filed on Nov. 10, 2008.
Japanese Patent Office Communication. Apr. 21, 2009, 3 pp. (includes statement submitted by third party).
Submission of Publications and the like, dated Mar. 24, 2009, in Japanese Patent Application No. 2004-130373. (with English translation).

(Continued)

*Primary Examiner* — Eisa Elhilo
(74) *Attorney, Agent, or Firm* — Oblon, Spivak, McClelland, Maier & Neustadt, L.L.P.

(57) ABSTRACT

A two-part hair dye composed of a first part containing an alkali agent, a second part containing hydrogen peroxide, and a non-aerosol foamer container for discharging a liquid mixture of the first part and the second part in the form of a foam, the liquid mixture containing the following components (A) and (B): (A) a polymer or copolymer containing 70% or more mole fraction of diallyldimethyl quaternary ammonium salt monomer, and (B) an N-acylamino acid salt, an N-acyl-N-alkylamino acid salt, or an ether carboxylic acid salt, wherein, an equivalent ratio of the anion site of the component (B) to the cation site of the component (A) (anion/cation) is more than 1.

20 Claims, No Drawings

FOREIGN PATENT DOCUMENTS

| | | |
|---|---|---|
| JP | 62-242609 | 10/1987 |
| JP | 63-246313 | 10/1988 |
| JP | 04-99711 | 3/1992 |
| JP | 04-282307 | 10/1992 |
| JP | 04-282308 | 10/1992 |
| JP | 04-293568 | 10/1992 |
| JP | 06-107530 | 4/1994 |
| JP | 06-271435 | 9/1994 |
| JP | 6-271435 | 9/1994 |
| JP | 07-23293 | 3/1995 |
| JP | 07-267834 | 10/1995 |
| JP | 07-330559 | 12/1995 |
| JP | 07-330560 | 12/1995 |
| JP | 08-40837 | 2/1996 |
| JP | 8-119838 | 5/1996 |
| JP | 08-119839 | 5/1996 |
| JP | 08-165235 | 6/1996 |
| JP | 08-199188 | 8/1996 |
| JP | 8-199188 | 8/1996 |
| JP | 08-230959 | 9/1996 |
| JP | 08-231345 | 9/1996 |
| JP | 8-231346 | 9/1996 |
| JP | 08-259426 | 10/1996 |
| JP | 8-259426 | 10/1996 |
| JP | 08-268848 | 10/1996 |
| JP | 8-283695 | 10/1996 |
| JP | 09-2923 | 1/1997 |
| JP | 09-2925 | 1/1997 |
| JP | 9-25223 | 1/1997 |
| JP | 09-40534 | 2/1997 |
| JP | 2579516 | 2/1997 |
| JP | 09-136818 | 5/1997 |
| JP | 09-143040 | 6/1997 |
| JP | 09-506130 | 6/1997 |
| JP | 09-227347 | 9/1997 |
| JP | 9-227347 | 9/1997 |
| JP | 09-234112 | 9/1997 |
| JP | 9-255541 | 9/1997 |
| JP | 09-255541 | 9/1997 |
| JP | 9-301835 | 11/1997 |
| JP | 09-301835 | 11/1997 |
| JP | 10-25230 | 1/1998 |
| JP | 10-167938 | 6/1998 |
| JP | 10-287534 | 10/1998 |
| JP | 10-324357 | 12/1998 |
| JP | 11-18836 | 1/1999 |
| JP | 11-18837 | 1/1999 |
| JP | 11-50089 | 2/1999 |
| JP | 11-124321 | 5/1999 |
| JP | 11-139945 | 5/1999 |
| JP | 11-199454 | 7/1999 |
| JP | 11-206454 | 8/1999 |
| JP | 11-246369 | 9/1999 |
| JP | 11-286421 | 10/1999 |
| JP | 11-349453 | 12/1999 |
| JP | 2000-191471 | 7/2000 |
| JP | 2000-128215 | 9/2000 |
| JP | 2000-297018 | 10/2000 |
| JP | 2000-297019 | 10/2000 |
| JP | 2001-10930 | 1/2001 |
| JP | 2001-19626 | 1/2001 |
| JP | 2001-39460 | 2/2001 |
| JP | 2001-97834 | 4/2001 |
| JP | 2001-172166 | 6/2001 |
| JP | 2001-278742 | 10/2001 |
| JP | 2001-288054 | 10/2001 |
| JP | 2001-327321 | 11/2001 |
| JP | 2002-20247 | 1/2002 |
| JP | 2002-97121 | 4/2002 |
| JP | 2002-154938 | 5/2002 |
| JP | 2002-193771 | 7/2002 |
| JP | 2002-220329 | 8/2002 |
| JP | 2002-226340 | 8/2002 |
| JP | 2002-226344 A | 8/2002 |
| JP | 2002-284655 | 10/2002 |
| JP | 03-12479 | 1/2003 |
| JP | 2003-26554 | 1/2003 |
| JP | 2003-40747 | 2/2003 |
| JP | 2003-63936 | 3/2003 |
| JP | 2003-73240 | 3/2003 |
| JP | 2003-73241 | 3/2003 |
| JP | 2003-081791 A | 3/2003 |
| JP | 2003-95900 | 4/2003 |
| JP | 2003-192551 | 9/2003 |
| JP | 2004-075644 | 3/2004 |
| JP | A1-2007-291015 | 11/2007 |
| JP | A1-2007-314523 | 12/2007 |
| JP | 2010-6803 | 1/2010 |
| JP | 2010-6805 | 1/2010 |
| WO | WO 91/14759 | 10/1991 |
| WO | WO 95/16023 | 6/1995 |
| WO | WO 01/85105 | 11/2001 |
| WO | WO 01/85113 | 11/2001 |

OTHER PUBLICATIONS

Submission of Publication and the like, dated Sep. 7, 2009, in Japanese Patent Application No. 2004-130373.
Shinbiyo Marcel. Oct. 1996. No. 31, pp. 73 and 83. Vivid Highlight advertisement page (with partial English translation).
Vivid Highlight. Iriya Cosmetics. Packaging and Instructions Insert. Sep. 6, 1996 (with English translation).
Hair Mode. Aug. 1996. No. 437, p. 108. (with partial English translation).
Decision to Refuse a European Patent Application issued Apr. 19, 2011, in regard to European Patent Application No. 08752171.2, filed Apr. 25, 2008.
Third-Party Observation submitted Jun. 3, 2011, in European Patent Application No. 10172766.7, filed Apr. 26, 2004.
Rompps Chemie Lexikon, vol. 6, 8$^{th}$ Ed. 1998. p. 4531.
Third-Party Observation submitted May 3, 2011, in European Patent Application No. 0 400 9836.0.
Extended European Search Report issued Apr. 7, 2011, in European Application No. 10183376.2.
European Patent Office Communication pursuant to Rule 114(2) EPC issued May 3, 2011, in European Application No. 04009836.0 filed Apr. 26, 2004.
Third-Party Observation filed on Apr. 27, 2011, in European Patent Application No. 0 400 9836.0 (including translation of submission).
Food and Packaging. vol. 34, No. 8. "Can Technology Study Group." Aug. 1, 1993. 6 pages.
Notification of Reason for Refusal, dated Jul. 22, 2008, in Japanese Patent Application No. 2004-130373.
English translation of Submission of Publication and the like, dated Dec. 25, 2007, in Japanese Patent Application No. 2004-130373.
English translation of Submission of Publication and the like, dated Feb. 29, 2008, in Japanese Patent Application No. 2004-130373.
Extended European Search Report issued in Nov. 4, 2010 in European Patent Application No. 10172766.7.
Taya-A.T. HM Education Mook., Series 3. "Knowing Mechanisms of Hair Coloring Agents." Apr. 10, 1998. pp. 8-9. (with English translation).
Nakanishi, Fumio. Fragrance Journal. "Future View of Hair Care Products." Jan. 15, 1997. pp. 49-56. (with English translation).
Sato, Takatoshi, et al. Fragrance and Cosmetics Science. "Permanent Hair Colorant." Sep. 20, 2001. pp. 138-140. (with English translation).
Watanabe, Yasushi, et al. Hair Science. "Hair Colorant." Feb. 1, 1986. pp. 144-150. (with English translation).
Submission of Publications and the like, filed Oct. 18, 2010 in Japanese application No. 2004-130373 (w/ English Translation).
Communication Pursuant to Article 94(3) EPC issued Nov. 5, 2010 in European Patent application No. 0 400 9836.0.
Submission of Publications and the like, filed Oct. 25, 2010 in Japanese application No. 2008-270377 (w/ English Translation).
Decision of Refusal issued Jun. 16, 2010 in Japanese application No. 2004-130373 (w/ English Translation).
Written Demand for Appeal filed Sep. 10, 2010 in Japanese application No. 2004-130373 (w/ English Translation).
Amendment filed Sep. 10, 2010 in Japanese application No. 2004-130373 (w/ English Translation).

Submission of Publications and the like, filed Apr. 8, 2009 in Japanese application No. 2004-130373 (w/ English Translation).
English Translation of Decision to Grant a Patent issued Jan. 4, 2011 in Japanese Patent application No. 2004-130373 w/ Allowed Claims.
English Translation of Decision to Grant a Patent issued Jan. 4, 2011 in Japanese Patent application No. 2008-270377 w/ Allowed Claims.
English translation of Remarks filed Oct. 20, 2008 in Japanese application No. 2004-130373.
English translation of Remarks filed Mar. 9, 2009 in Japanese application No. 2004-130373.
English translation of Amendment filed Mar. 9, 2009 in Japanese application No. 2004-130373.
European Search Report submitted Aug. 23, 2004, in European Patent Application No. 04009836.0.
English translation of Submission of Publications filed Nov. 10, 2008 in Japanese application No. 2004-130373.
English translation of Notification of Reasons for Refusal issued Jan. 6, 2009 in Japanese application No. 2004-130373.
English translation of Submission of Publications filed Dec. 25, 2007 in Japanese application No. 2004-130373.
English translation of Submission of Publications filed Feb. 29, 2008 in Japanese application No. 2004-130373.
Response to Communication Pursuant to Article 96(2) EPC filed Apr. 25, 2007 in European Patent application No. 0 400 9836.0.
Communication Pursuant to Article 94(3) EPC issued Dec. 29, 2008 in European Patent application No. 0 400 9836.0.
Response to Communication filed Jul. 8, 2009 in European Patent application No. 0 400 9836.0.
Third-Party Observation filed on Dec. 19, 2009 in European Patent application No. 0 400 9836.0.
Observations under Rule 114(2) EPC filed Apr. 9, 2010 in European Patent application No. 0 400 9836.0.
Third-Party Observation filed on May 10, 2010 in European Patent application No. 0 400 9836.0.
Communication Pursuant to Article 94(3) EPC issued Jun. 28, 2010 in European Patent application No. 0 400 9836.0.
Response to Communication filed Aug. 10, 2010 in European Patent application No. 0 400 9836.0.
Amendment filed Dec. 5, 2008 in European Patent application No. 0 400 9836.0.
Response to Communication filed Feb. 18, 2011 in European Patent application No. 0 400 9836.0.
Remarks filed Feb. 25, 2011 in European Patent application No. 08 752 171.2.
Experimental Report 1 (with English translation), served on May 24, 2011, in regard to Heisei 23 year (Yo) No. 22009.
Nakanishi, Fumio. Fragrance Journal. "Function of Recent Hair Coloring Agent and Developmental Trend Thereof." Aug. 15, 2001. pp. 39-45. (with English translation).
Yamagata, Yoshifumi, et al. Fragrance Journal. "Science of Foam: Function and Physical Properties of Foam." Dec. 15, 1992. pp. 37-47. (with English translation).
Yamakawa, Arata, et al. Fragrance Journal. "Development and Objective of Mousse Hair Cosmetic Products." Dec. 15, 1992. pp. 48-54. (with English translation).
Tashima, Masaru, et al. Fragrance Journal. "Research and Development of Mist Foam Type Hair Styling Product." Dec. 15, 1992. pp. 61-69. (with English translation).
Omura, Takayuki, et al. Fragrance Journal. "Development Trend and Problems of Recent Hair Foam." Mar. 15, 1994. pp. 29-35. (with English translation).
Miyagi, Takashi. Food and Packaging, vol. 34, No. 8. "Does Non-Gas Container Cause a Boom? (Part 2)" 1993. pp. 467-471. (with English translation).
Miyagi, Takashi. Food and Packaging, vol. 36, No. 3. Non-Gas Container Having Increased Level of Accomplishment (Part 3). 1995. pp. 154-158. (with English translation).
Prettia Product Information (with English Translation), Kao Corporation, published after Apr. 23, 2003. (served on May 25, 2011 in regard to Heisei 23 year (Yo) No. 22009).
Instructions for Feminine Treatment Hair Color (with English Translation), Feminine Co., Ltd., published before Apr. 23, 2003 (served on May 25, 2011 in regard to Heisei 23 year (Yo) No. 22009).

Feminine Treatment Hair Color 84, Certification for Approval for Manufacture of Quasi-Drug (with English Translation), Jan. 30, 1997.
Instructions for Feminine Retouch Color (with English Translation), Feminine Co., Ltd., published before Apr. 23, 2003. (served on May 25, 2011, in regard to Heisei 23 year (Yo) No. 22009).
Experimental Report 2 (with English translation), served on May 25, 2011, in regard to Heisei 23 year (Yo) No. 22009.
Experimental Report 3 (with English translation), served on May 25, 2011, in regard to Heisei 23 year (Yo) No. 22009.
Test Report 4 (with English translation), served on Jul. 10, 2011, in regard to Heisei 23 year (Yo) No. 22009.
Mottram, F.J., et al. Poucher's Perfumes, Cosmetics and Soaps, $10^{th}$ ed. © 2000. "Hair Shampoos." pp. 295-301.
Handbook "Poly Haarberater Coloration," original edition, 1992. pp. 76-77.
Third-Party Observation submitted May 12, 2011, in European Patent Application No. 04009836.0.
371-EPO Response in European Patent Application No. 04009836.0, Jul. 15, 2011.
Reply to EESR in European Patent Application No. 10172766.7, Apr. 29, 2011.
Third-Party Observation submitted Jun. 24, 2011, in European Patent Application No. 10172766.7.
Third-Party Observation submitted Jun. 24, 2011, in European Patent Application No. 10183376.2.
Photocopy of a folding, collapsible box for "Poly Brillance Intensiv-Color-Creme", dated as Aug. 25, 1997.
Instructions for use contained in the folding, collapsible box for "Poly Brillance Intensiv-Color-Crème" Aug. 25, 1997.
Entire contents of the folding, collapsible box for "Poly Brillance Intensiv-Color-Crème" Aug. 25, 1997.
Close-up photocopy of the folding, collapsible box for "Poly Brillance Intensiv-Color-Crème" Aug. 25, 1997.
Miyagi, Takashi. Food and Packaging, vol. 42, No. 10. "Growing Pump Foamer Spreading into Western Markets, Part One: Mini-Foamer." Oct. 1, 2001. pp. 609-613. (with English translation).
Kishi, Haruo. Modern Fragrance and Cosmetics Science, $1^{st}$ Edition. Mar. 20, 1979. pp. 42-47. (with English translation).
Cosmetics Handbook. Nov. 1, 1996. pp. 220-221, 441-444. (with English translation).
Handbook—Raw Materials of Cosmetics and Drugs—revised edition. Feb. 1, 1977. pp. 358-361. (with English translation).
Yasuda, Kosaku, et al. Knowledge of Fat and Oil Products. Aug. 25, 1977. pp. 240-244. (with English translation).
Mitsui, Takeo. New Cosmetic Science. Jan. 12, 1993. pp. 137-142. (with English translation).
The Handbook of Oil Chemistry, $4^{th}$ ed. "Lipids and Surfactants." Nov. 20, 2001. p. 522. (with English translation).
Comprehensive Dictionary of Chemistry. Oct. 20, 1989. pp. 56, 60-61, 646-647, 1762-1763. (with English translation).
Sato, Takatoshi, et al. Fragrance and Cosmetics Science. Mar. 20, 1997. pp. 73-74. (with English translation).
Japanese Collection of General Raw Materials for Cosmetics, fourth edition. Oct. 31, 1997. p. 583. (with English translation).
Analytical Chemistry Handbook, revised second edition. Oct. 10, 1971. pp. 27-29. (with English translation).
Analysis Methods for Surfactants. Oct. 1, 1975. pp. 117-118. (with English translation).
Chemical Daily. "Surfactant—Penetrated to the various fields taking advantage of unique characteristics." Jan. 21, 1999. (with English translation).
The Nikkan Kogyo Shimbun, Ltd. "Nonylphenol Identified as Endocrine Disrupting Chemical." Aug. 6, 2001. (with English translation).
Chemical Daily. "Surfactant—Started growing responding to safety requirement." Jan. 19, 2000. (with English translation).
Chemical Daily. "Surfactant—Remarkable performance of non-ionic surfactant (Market conditions in chemicals)." Jan. 25, 2002. (with English translation).
Nakanishi, Fumio, et al. Science History of Hair Dye. Jan. 8, 1991. pp. 45-47. (with English translation).
Experiment Result Report 1 (with English translation), prepared on Jul. 11, 2011, in regard to No. 22009, 2011 (yo).

Experimental Result Report 2 (with English translation), prepared on Jul. 22, 2011, in regard to No. 22009, 2011 (yo).
Declaration by Akiko Nagabuchi (with English translation), served on Sep. 21, 2011, in regard to No. 22009, 2011 (yo).
Experiment Result Report 5 (with English translation), served on Sep. 21, 2011, in regard to No. 22009, 2011 (yo).
Arai, Yasuhiro. "State-of-the-art: Hair Color Technology—Trends in development as seen in patents." Published by Fragrance Journal Ltd. Aug. 25, 2004. pp. 102-105, 212-213. (with English translation).
Experimental Result Report 6 (with English translation), served on Sep. 21, 2011, in regard to No. 22009, 2011 (yo).
Experimental Result Report 7 (with English translation), served on Sep. 21, 2011, in regard to No. 22009, 2011 (yo).
Hayakawa, Masakatsu. Fragrance Journal. "Trends in the R&D of Hair Dyes and Issues to Address." No. 38 (vol. 7, No. 5) Sep. 25, 1979. pp. 41-44. (with English translation).
Written Argument filed by the Debtor (1/2) in the Case of Request for Provisional Disposition of Patent Right: No. 22056, 2011 (yo), served on Sep. 6, 2011. pp. 1-5, 29-34. (with partial English translation).
Amendments to the Claims in Japanese Patent Application No. 2010-268209, filed on Apr. 8, 2011. (with English translation).
Publication of Unexamined Patent Application JP 2003-81369, Mar. 19, 2003.
English translation of Submission of Publications and the like, filed Mar. 24, 2009, in Japanese Application No. 2004-130373.
English translation of Submission of Publications and the like, filed Nov. 10, 2008, in Japanese Application No. 2004-130373.
English translation of Notification of Reasons for Refusal issued Jul. 22, 2008, in Japanese Application No. 2004-130373.
English translation of Submission of Publications and the like, filed Sep. 7, 2009, in Japanese Application No. 2004-130373.
English translation of Submission of Publications and the like, filed Feb. 29, 2008, in Japanese Application No. 2004-130373.
English translation of Submission of Publications and the like, filed Dec. 25, 2007, in Japanese Application No. 2004-130373.
Comprehensible Surfactant, first edition. Sep. 1, 2003. pp. 32-49. (with English translation).
Quasi Drugs Manufacturing Material Specification 2006, first edition. pp. 527-528. Jun. 16, 2006. (with English translation).
Nakanishi, Fumio. Fragrance Journal. "Recent Progress and Prospective Problems in Hair Colorants and Hair Lighteners" vol. 25, No. 1. Jan. 15, 1997. pp. 49-56. (with English translation).
Sato, Takatoshi. Science of Cosmetics. Mar. 20, 1997. pp. 138-140. (with English translation).
Denavarre, Maison G. The Chemistry and Manufacture of Cosmetics, second edition, vol. 4. 1975. pp. 841-863.
Cosmetics Dictionary, first edition. Oct. 1, 1992. p. 373. (with English translation).
New Cosmetic Science, second edition. Jan. 18, 2001. pp. 152-153. (with English translation).
"Make Your Hair Beautiful by Correct Usage—Hair Coloring ABC, revised edition." Feb. 1, 2000. pp. 18-19. (with English translation).
Robbins, Clarence R. "Chemical and Physical Behavior of Human Hair, fourth edition." Jul. 10, 2006. pp. 221-231. (with English translation).
Experimental Result Report 8 (with English translation), served on Nov. 29, 2011, in regard to No. 22009, 2011 (yo).
Fragrance Journal. vol. 19, No. 6. "Recent Progress of Hair Dyes and Problems in Research and Development." Jun. 15, 1991. pp. 26-27. (with English translation).
Miyagi, Takashi. Food and Packaging, vol. 34, No. 9. "Will Non-Gas Containers Create a Boom? (No. 3)" 1993. pp. 531-535. (with English translation).
Extended Search Report issued Nov. 4, 2010, in European Application No. 10172766.7.
Submission of Publication issued Oct. 18, 2010, in JP Application No. 2004-130373 (with English translation).
Office Action issued Nov. 5, 2010, in EP Application No. 04 009 836.0.
Third Party Observation issued on May 3, 2011, in corresponding European Application No. 04 009 836.
Iwakura, Ryouhei. "Present State and Problems of Hair Dyes." Fragrance Journal, Special Issue. No. 11, pp. 87-93. Dec. 25, 1990. (with English translation).
Ishikawa, Ryoji. Experimental Report, in regard to No. 22056, 2011 (yo). Dec. 28, 2011 (with English translation).
Declaration by Hattori, Nobuhito, in regard to No. 22056, 2011 (yo), served on Dec. 28, 2011 (with English translation).
Unichemy Corp. Experimental Report, in regard to No. 22056, 2011 (yo). Issued on Jun. 24, 2011 (with English translation).
Pharmaceutical Additive Dictionary, $2^{nd}$ edition. pp. 153-154, 203-205. Mar. 25, 2002. (with English translation).
Murata, Seishiro. Cosmetic Dictionary, $1^{st}$ edition. pp. 182-183, 666-667. Dec. 15, 2003. (with English translation).
Miyagi, Takashi. Food and Container, vol. 35, No. 10. pp. 588-593. 1994. (with English translation).
Miyagi, Takashi. Food and Container, vol. 35, No. 11. pp. 624-627. 1994. (with English translation).
Henkel Study Report, Study No. 1100546-2. "Single Application Epicutaneous Patch Test ($24^{th}$ Patch Test)," served on Jan. 30, 2012, in regard to No. 22009, 2011 (yo).
Henkel Study Report, Study No. 1100546-1. "Open Epicutaneous Test," served on Jan. 30, 2012, in regard to No. 22009, 2011 (yo).
Henkel Study Report. "In Vitro Skin Irritation Test: Human Skin Model Test," served on Jan. 30, 2012, in regard to No. 22009, 2011 (yo).
Study Report, No. 1100547-1, "Dermatological Use Test with Hair-Coloring Products in Split Design," served on Jan. 30, 2012, in regard to No. 22009, 2011 (yo).
Experimental Result Report 13 (with English translation), served on Jan. 30, 2012, in regard to No. 22009, 2011 (yo).
Excerpt from the Internet Website: www.bagonvalve.com in regard to Request Cancelation in Utility Model 20 2004 021 775, served on Apr. 18, 2012, (3 pp.).
Dr. Matthias Schweinsberg, Test Report : Foaming Characteristics and Flow Characteristics of Cosmetic Products According to EP 1 291 006 A1, Feb. 17, 2012 with English Translation, served on Apr. 17, 2012 in regard to DE litigation No. 4a O28/11.
Test Report dated May 1, 2012, Hoyu Co., Ltd., Product Development Laboratory of General Research & Development Institute, Section Chief: Ryouji Ishikawa, served on May 11, 2012 in regard to No. 5260, 2012 (wa) with English translation, (13 pp.).
European Patent Office Communication issued Mar. 12, 2012 in European Patent Application 04 009 836.0.
U.S. Appl. No. 13/439,429, filed Apr. 4, 2012, Fujinuma, et al.
U.S. Appl. No. 13/509,735, filed May 14, 2012, Naoi, et al.
Chinese Office Action issued Oct. 8, 2012 in corresponding Chinese Patent Application No. 201080007865.0 with English translation (11 pp.).

* cited by examiner

TWO-PART HAIR DYE

The present application is a continuation of U.S. application Ser. No. 13/146,157, filed Jul. 25, 2011, now U.S. Pat. No. 8,349,022 B2 which is a National Stage (371) of PCT/JP2010/001627, filed Mar. 9, 2010, and claims priority to JP 2009-058763, filed on Mar. 11, 2009, and JP 2009-280282, filed Dec. 10, 2009.

FIELD OF THE INVENTION

The present invention relates to a two-part hair dye.

BACKGROUND OF THE INVENTION

Conventionally, a hair bleach product and a hair dye product are widely available in the form of liquid or cream. However, it is difficult for those who are not accustomed to using such a product to evenly apply it to the hair. This is because the viscosity of a mixture to be applied to the hair is adjusted relatively high, namely, to approximately 1,000 to 10,000 mPa·s, for prevention of dripping while the mixture is left on the hair. This makes it difficult to evenly spread the mixture and to adequately cover the hair root with the mixture. Furthermore, skills such as blocking and two-mirror technique are necessary for application of the mixture to the hair root and the back of the head, also requiring much time.

In contrast, a non-aerosol type foamer container discharging a liquid mixture of a two-part hair bleach or a two-part hair dye contained therein in the form of a foam is proposed (Patent Document 1). The above hair bleach product or hair dye product discharges a liquid mixture of the first part and the second part from a non-aerosol type foamer container in the form of a foam, whereby the liquid mixture is evenly applied to the hair, resulting in an evenly-colored finish. The above hair bleach product or hair dye product is particularly useful for resolving color differences between a newly-grown part and an already-dyed part. For these reasons, it is supported by a wide range of customers, regardless of sex and age groups.

However, the two-part hair bleach and the two-part hair dye in the form of a foam of Patent Document 1 have various problems peculiar to the product in the form of a foam discharged from a non-aerosol type foamer container such as reduced foaming properties at low temperature. Also, because such a hair dye product has extremely lower viscosity in the state of a liquid mixture as compared to a conventional liquid or cream (hereinbelow, referred to as "conventional type") hair dye product, there has also been a limitation that a composition having good storage stability has to be designed. Furthermore, the two-part hair bleach and the two-part hair dye in the form of a foam of Patent Document 1 tend to have less sufficient fastness to shampooing than does a conventional type. This is considered to be attributable to the following reasons: because the hair dye product is applied to the hair in the form of a foam, the amount of the hair dye directly contributing to dyeing is smaller than the amount of the hair dye actually applied, and also, because the area of the air-liquid surface of the above product is larger than that of a conventional type, ammonia serving as an alkali agent readily volatilizes, leading to an insufficient amount of the alkali agent for full penetration of the dye into the center of the hair.

In contrast, as a conventional type two-part hair dye, a two-part hair dye containing polyoxyalkylenated carboxylic acid ether or a salt thereof and a cationic polymer or an amphoteric polymer having no less than a certain level of cationic charge density is proposed (refer to Patent Document 2). According to this literature, the two-part hair dye disclosed therein can impart a favorable hue. However, there is no description pertaining to a two-part hair dye provided in the form of a foam by using a non-aerosol type foamer container discharging a liquid mixture contained therein. Further, this literature is also totally unsuggestive of a problem peculiar to the two-part hair dye in the form of a foam such as low foaming properties at low temperature and a problem peculiar to a two-part hair dye prepared in the aforementioned form such as storage stability and fastness to shampooing.

Also, a less irritating shampoo composition containing alkyl ether acetate and a cationic polymer exhibiting excellent hair color fading-preventing effects, foaming, smoothness when running fingers through the hair while shampooing, and smoothness during rinsing is proposed (Patent Document 3). However, this literature neither describes nor suggests the mole fraction of the cationic monomer in the cationic polymer. Further, provided that this literature pertains to an invention relating to a shampoo composition, there is no question that it is totally silent on application to a hair dye product. In the first place, this invention relates to a technique to achieve prevention of color fading of the hair dyed with a hair color by use of this shampoo composition, and irrespective of the shampoo used, the technical idea per se is entirely unrelated to provision of a hair dye product excellent in fastness to shampooing.

[Patent Document 1] JP-A-2004-339216
[Patent Document 2] JP-A-2003-192551
[Patent Document 3] JP-A-2001-131034

SUMMARY OF THE INVENTION

The present invention provides a two-part hair dye which contains a first part containing an alkali agent, a second part containing hydrogen peroxide, and a non-aerosol foamer container for discharging a liquid mixture of the first part and the second part in the form of a foam, the liquid mixture containing the following components (A) and (B):

(A) a polymer or copolymer containing 70% or more mole fraction of diallyldimethyl quaternary ammonium salt monomer, and (B) an N-acylamino acid salt, an N-acyl-N-alkylamino acid salt, or an ether carboxylic acid salt, wherein, an equivalent ratio of the anion site of the component (B) to the cation site of the component (A) (anion/cation) is more than 1, and a viscosity of the liquid mixture at 25° C. is 1 to 300 mPa·s.

DETAILED DESCRIPTION OF THE INVENTION

The present invention relates to a two-part hair dye provided in the form of a foam by using a non-aerosol foamer container. This hair dye product has good storage stability and dyeability, while taking advantage of the merit of the two-part hair dye in the form of a foam described in Patent Document 1. After dyeing, the hair dye product exhibits excellent fastness also to shampooing, which is said to be likely to cause color fading.

The present inventors found that the aforementioned problems can be resolved by using a polymer or copolymer containing not less than a certain ratio of diallyldimethyl quaternary ammonium salt monomer in combination with a specific anionic surfactant.

[(A): Polymer or Copolymer Containing 70% or More Mole Fraction of Diallyldimethyl Quaternary Ammonium Salt Monomer]

The polymer or copolymer of Component (A) improves fastness to shampooing by separation of complexes formed when a liquid mixture of the first part and the second part is diluted with water through interaction with Component (B). In view of the above, the mole fraction of the diallyldimethyl quaternary ammonium salt monomer needs to be not less than 70%. The mole fraction is more preferably not less than 80%, and even more preferably not less than 90%. In the case of a copolymer, no limitation is imposed on other monomers as long as they are copolymerizable; however, they preferably contain acrylic acid or acrylamide. Examples of such a polymer or copolymer include, as a commercially available product, Merquat 100 (mole fraction: 100%) and Merquat 295 (mole fraction: 95%) (the products of Nalco Company).

The content of Component (A) in a liquid mixture of the first part and the second part is preferably 0.1 to 1.5 mass %, more preferably 0.15 to 1.2 mass %, and even more preferably 0.2 to 1 mass %. Also, the cationic polymer or the amphoteric polymer of Component (A) may be contained in either the first part or the second part.

[(B): N-acylamino Acid Salt, N-acyl-N-alkylamino Acid Salt, or Ether Carboxylic Acid Salt]

The N-acylamino acid salt, the N-acyl-N-alkylamino acid salt, or the ether carboxylic acid salt of Component (B) improves fastness to shampooing through complexes formed by interaction with Component (A) when a liquid mixture of the first part and the second part is diluted with water.

At this point, examples of an amino acid residue of the N-acylamino acid salt include glutamic acid and aspartic acid, and examples of an amino acid residue of the N-acyl-N-alkylamino acid salt include glutamic acid, glycine, and β-alanine. Also, examples of an alkyl group of the N-acyl-N-alkylamino acid salt include a methyl group, an ethyl group, a propyl group, and an isopropyl group. Also, examples of an acyl group include a lauroyl group, a myristoyl group, and a palmitoyl group, and examples of the N-acylamino acid salt and the N-acyl-N-alkylamino acid salt include a sodium salt, a potassium salt, a lithium salt, an ethanolamine salt, a diethanolamine salt, and a triethanolamine salt (hereinbelow, abbreviated as TEA). Preferred specific examples of the N-acylamino acid salt include N-lauroyl glutamate, N-myristoyl glutamate, N-stearoyl glutamate, N-cocoyl glutamate, and N-hydrogenated tallow glutamate, and preferred specific examples of the N-acyl-N-alkylamino acid salt include an N-lauroyl-N-isopropyl glycine salt, an N-lauroyl sarcosine salt, an N-myristoyl sarcosine salt, an N-palmitoyl sarcosine salt, and an N-lauroyl-N-methyl-β-alanine salt.

Examples of the ether carboxylic acid salt include a polyglyceryl alkyl ether acetic acid salt or an ether acetic acid salt represented by the following general formula (I):

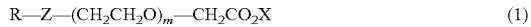

$$R\text{—}Z\text{—}(CH_2CH_2O)_m\text{—}CH_2CO_2X \quad (1)$$

wherein, R represents a linear or branched alkyl group or alkenyl group having a carbon number of 7 to 19, Z represents —O— or —CONH—, X represents a hydrogen atom, an alkali metal, triethanolamine, or ammonium, and m represents a number of 1 to 20.

In the aforementioned ether acetic acid salt, the carbon number of R is preferably 11 to 15. Also, m is preferably 3 to 15, more preferably 6 to 12. Specific examples thereof include polyoxyethylene (10) lauryl ether acetic acid (in the general formula (I), $R=C_{12}H_{25}$, $Z=$—O—, m=10), polyoxyethylene (8) myristyl ether acetic acid (in the general formula (I), $R=C_{14}H_{29}$, $Z=$—O—, m=8), lauric acid amide polyoxyethylene (6) ether acetic acid (in the general formula (I), $R=C_{11}H_{23}$, $Z=$—CONH—, m=6), and lauric acid amide polyoxyethylene (10) ether acetic acid (in the general formula (I), $R=C_{11}H_{23}$, $Z=$—CONH—, m=10). Also, the degree of neutralization of the ether acetic acid salt is preferably 60 to 120%, and the counter ion X is preferably an alkali metal, more preferably potassium. Examples of the ether acetic acid salt include a polyoxyethylene tridecyl ether acetic acid salt and a polyoxyethylene lauryl ether acetic acid salt, and examples of the salt thereof include a sodium salt and a potassium salt.

The content of Component (B) in a liquid mixture of the first part and the second part is preferably 0.5 to 5 mass %, more preferably 0.7 to 4.5 mass %, and even more preferably 1 to 3.5 mass %. Also, the N-acylamino acid salt, the N-acyl-N-alkylamino acid salt, or the ether carboxylic acid salt of Component (B) may be contained in either the first part or the second part, regardless of whether Component (A) is contained in the first part or the second part.

[Ratio of Component (B) to Component (A)]

The ratio of Component (B) to Component (A) in a liquid mixture of the first part and the second part is adjusted such that the equivalent ratio of the anion site of the component (B) to the cation site of the component (A) (anion/cation) is more than 1, taking into consideration that the content is stably present without separation when the first part and the second part are mixed, while it separates when the mixture is diluted with water. Further, the ratio of Component (B) to Component (A) is preferably adjusted such that the equivalent ratio is 1.1 to 20, more preferably 1.2 to 10.

[Alkali Agent]

The first part contains an alkali agent. Examples of the alkali agent include ammonia and a salt thereof; alkanolamine such as monoethanolamine, isopropanolamine, 2-amino-2-methyl propanol, and 2-aminobutanol, and a salt thereof; alkanediamine such as 1,3-propanediamine and a salt thereof; and carbonate such as guanidine carbonate, sodium carbonate, potassium carbonate, sodium bicarbonate, and potassium bicarbonate. Two or more of these alkali agents may be used in combination, and the content thereof in a liquid mixture is preferably 0.05 to 15 mass %, more preferably 0.1 to 10 mass %, and even more preferably 0.2 to 5 mass %, from the viewpoints of adequate hair dyeing and bleaching effects and reduced hair damage and scalp irritation.

[Hydrogen Peroxide]

The content of hydrogen peroxide in the second part is preferably 1 to 9 mass %, more preferably 3 to 6 mass %, and the content of hydrogen peroxide in a liquid mixture of the first part and the second part is preferably 1 to 6 mass %, more preferably 2 to 5 mass %. Also, the pH of the second part is preferably 2 to 6, more preferably 2.5 to 4 in order to prevent decomposition of hydrogen peroxide.

[Dye]

The two-part hair dye of the present invention contains an oxidation dye intermediate or a direct dye in the first part.

(Oxidation Dye Intermediate)

Publicly known precursors and couplers normally used in a hair dye product can be used as the oxidation dye intermediate. Examples of the precursor include para-phenylenediamine, toluene-2,5-diamine, 2-chloro-para-phenylenediamine, N-methoxyethyl-para-phenylenediamine, N,N-bis(2-hydroxyethyl)-para-phenylenediamine, 2-(2-hydroxyethyl)-para-phenylenediamine, 2,6-dimethyl-para-phenylenediamine, 4,4'-diaminodiphenylamine, 1,3-bis(N-(2-hydroxyethyl)-N-(4-aminophenyl)amino)-2-propanol, PEG-3,3,2'-para-phenylenediamine, para-aminophenol, para-methylaminophenol, 3-methyl-4-aminophenol, 2-aminomethyl-4-aminophenol, 2-(2-hydroxyethylaminomethyl)-4-aminophenol, ortho-aminophenol, 2-amino-5-methylphenol, 2-amino-6-methylphenol, 2-amino-5-acetamide phenol, 3,4-diaminobenzoic acid, 5-aminosalicylic acid, 2,4,5,6-tetraminopyrimidine, 2,5,6-triamino-4-hydroxypyrimidine, 4,5-diamino-1-(4'-chlorobenzyl)pyrazole, 4,5-diamino-1-hydroxyethylpyrazole, and salts of these substances.

Also, examples of the coupler include meta-phenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, meta-aminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-meta-aminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, 2,6-diaminopyridine, and salts of these substances.

Two or more of each of the precursor and the coupler can be used in combination, and the content of each of them in the liquid mixture is preferably 0.01 to 5 mass %, more preferably 0.1 to 4 mass %.

(Direct Dye)

Examples of the direct dye include an acid dye, a nitro dye, a disperse dye, and a basic dye. Examples of the acid dye include Blue No. 1, Violet No. 401, Black No. 401, Orange No. 205, Red No. 227, Red No. 106, Yellow No. 203, and Acid orange No. 3. Examples of the nitro dye include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue No. 2, HC Orange No. 1, HC Red No. 1, HC Yellow No. 2, HC Yellow No. 4, HC Yellow No. 5, HC Red No. 3, and N,N-bis(2-hydroxyethyl)-2-nitro-p-phenylenediamine. Examples of the disperse dye include Disperse Violet 1, Disperse Blue 1, and Disperse Black 9. Examples of the basic dye include Basic Blue 99, Basic Brown 16, Basic Brown 17, Basic Red 76, Basic Red 51, Basic Yellow 57, Basic Yellow 87, and Basic Orange 31.

Two or more of the direct dye may be used in combination, and the direct dye may be used in combination with the oxidation dye intermediate. Also, the content of the direct dye in the liquid mixture is preferably 0.001 to 5 mass %, more preferably 0.01 to 3 mass %.

[Surfactant]

In order to impart good storage stability to the two-part hair dye of the present invention and allow easy formation of a stable foam through mixing of air and a hair cosmetic by foam discharge means of a foamer container, a surfactant other than Component (B) can be further added to either one or both of the first part and the second part. As the surfactant other than Component (B), any one of an anionic surfactant, a cationic surfactant, an amphoteric surfactant, and a nonionic surfactant other than Component (B) can be used.

Examples of the anionic surfactant other than Component (B) include a sulfuric acid ester surfactant such as alkyl sulfate and alkyl ether sulfate; a carboxylic acid surfactant such as a fatty acid salt, alkyl succinate, and alkenyl succinate; a phosphoric acid ester surfactant such as alkyl phosphate and alkyl ether phosphate; and a sulfonic acid surfactant such as sulfosuccinate, isethionate, a taurine salt, alkylbenzenesulfonic acid, α-olefin sulfonic acid, and alkanesulfonic acid. Preferred examples of the anionic surfactant other than Component (B) include alkyl sulfate and polyoxyalkylene alkyl sulfate, and the carbon number of the alkyl group of these surfactants is preferably 10 to 24, more preferably 12 to 18, and the alkyl group is preferably linear. Also, polyoxyalkylene alkyl sulfate is preferable, especially polyoxyethylene alkyl sulfate is more preferable. The average addition mole number of the oxyethylene group of the polyoxyalkylene alkyl sulfate is preferably 1 to 10, more preferably 2 to 5.

The cationic surfactant is preferably a mono long-chain alkyl quaternary ammonium salt. Specific examples thereof include cetrimonium chloride, steartrimonium chloride, behentrimonium chloride, stearalkonium chloride, and benzalkonium chloride. Among these, steartrimonium chloride and behentrimonium chloride are more preferable. Examples of a commercially available cationic surfactant include QUARTAMIN 86W, QUARTAMIN 86P CONC, QUARTAMIN 60W, and QUARTAMIN D2345P (the products of Kao Corporation), and NIKKOL CA-2580 (the product of Nihon Surfactant Kogyo K.K.).

Examples of the amphoteric surfactant include carbobetaine, amidobetaine, sulfobetaine, hydroxyl sulfobetaine, amidosulfobetaine, phospho-betaine, and imidazolinium surfactants having an alkyl group, an alkenyl group, or an acyl group with a carbon number of 8 to 24. Among them, a carbobetaine surfactant and a sulfobetaine surfactant are preferable. Preferred examples of the amphoteric surfactant include lauric acid amidopropyl betaine, coconut oil fatty acid amidopropyl betaine, lauryldimethylaminoacetic acid betaine, and laurylhydroxysulfobetaine.

Examples of the nonionic surfactant include an alkyl polyglucoside, a polyoxyalkylene alkyl ether, and an alkyl glyceryl ether. The carbon number of the alkyl group of the alkyl polyglucoside is preferably 8 to 18, more preferably 8 to 14, and even more preferably 9 to 11, and the alkyl group is preferably linear. The average degree of condensation of the glucoside is preferably 1 to 5, more preferably 1 to 2. The carbon number of the alkyl group of the polyoxyalkylene alkyl ether is preferably 10 to 22, more preferably 12 to 18, and the alkyl group is preferably linear. Also, the polyoxyethylene alkyl ether is more preferable, and especially the average addition mole number of the oxyethylene group of the polyoxyethylene alkyl ether is preferably 1 to 40, more preferably 4 to 30. The carbon number of the alkyl group of the alkyl glyceryl ether is preferably 8 to 18, more preferably 8 to 12, and the alkyl group is preferably branched.

Two or more of these surfactants other than Component (B) can be used in combination.

The content of the anionic surfactant other than Component (B) or the cationic surfactant in a liquid mixture of the first part and the second part is preferably 0 to 1 mass %, more preferably 0 to 0.8 mass %, and even more preferably 0 to 0.6 mass % so as not to affect the interaction between Component (A) and Component (B).

Also, the content of the amphoteric surfactant or the nonionic surfactant in a liquid mixture of the first part and the second part is preferably 0.1 to 5 mass %, more preferably 0.5 to 4 mass %, and even more preferably 1 to 3 mass %.

[Oil Agent]

From the viewpoint of stabilization of the foam of the liquid mixture discharged, the two-part hair dye of the present invention can further contain an oil agent. Examples of the oil agent include hydrocarbons such as squalene, squalane, liquid paraffin, liquid isoparaffin, and cycloparaffin; glycerides such as castor oil, cacao oil, mink oil, avocado oil, and olive oil; waxes such as bees wax, whale wax, lanoline, and carnauba wax; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut fatty acid, isostearic acid, and isopalmitic acid; higher alcohols such as myristyl alcohol, cetyl alcohol, stearyl alcohol, behenyl alcohol, 2-octyldodecanol, and cetostearyl alcohol; and further, isostearyl glyceryl ether and polyoxypropylene butyl ether. Among them, higher alcohols are preferable, of which myristyl alcohol, cetyl alcohol, and stearyl alcohol are preferable.

The content of the oil agent in a liquid mixture of the first part and the second part is preferably 0.01 to 3 mass %, more preferably 0.03 to 2.5 mass %, and even more preferably 0.05 to 2 mass %.

[Silicones]

From the viewpoint of long-time retention of the discharged foam, a liquid mixture of the first part and the second part of the two-part hair dye of the present invention preferably does not contain silicone. However, for smooth blending of foam into the hair and impartation of high conditioning effects to the hair, silicones can be further added within a certain range. Examples of the silicones include dimethylpolysiloxane, methylphenylpolysiloxane, polyether-modified silicone, amino-modified silicone, oxazoline-modified silicone elastomer, and emulsions of these silicones dispersed with a surfactant in water. Among them, polyether-modified silicone, amino-modified silicone, and emulsions of these silicones are preferable as they can stably disperse in water without using a viscosity enhancer.

The polyether-modified silicone includes end-modified silicone and side chain-modified silicone, for example, pendant-type (comb-type) silicone, both end-modified silicone, and one end-modified silicone. Examples of the modified silicone include a dimethylsiloxane-methyl(polyoxyethylene)siloxane copolymer, a dimethylsiloxane-methyl(polyoxypropylene)siloxane copolymer, and a dimethylsiloxane-methyl(polyoxyethylene-polyoxypropylene)siloxane copolymer. The polyether-modified silicone has an HLB of preferably 10 or higher, more preferably 10 to 18, in view of compatibility with water. Here, HLB is a value obtained from a phenol index (phenol index: an index correlated with HLB, applicable to an ether type nonionic surfactant).

Amino-modified silicone having an amino group or an ammonium group may be used as the amino-modified silicone, and amodimethicone is preferred.

When silicones are added to a liquid mixture of the first part and the second part, the content thereof is preferably no more than 2 mass %, more preferably 0.005 to 1 mass %, even more preferably 0.01 to 0.5 mass % for smooth blending of foam into the hair without impairing foaming properties, and for impartation of high conditioning effects to the hair.

[Solvent]

As a solvent, water and, if needed, an organic solvent are used in the two-part hair dye of the present invention. Examples of the organic solvent include lower alkanols such as ethanol and 2-propanol; aromatic alcohols such as benzylalcohol and benzyloxyethanol; polyols such as propylene glycol, 1,3-butanediol, diethylene glycol, and glycerin; cellosolves such as ethyl cellosolve, butyl cellosolve, and benzyl cellosolve; and carbitols such as ethyl carbitol and butyl carbitol.

[Other Arbitrary Components]

Besides the ones mentioned above, other components routinely used as cosmetic ingredients can be added to the two-part hair dye of the present invention. Examples of such an arbitrary component include animal and plant oil and fat, natural or synthetic polymers, ethers, protein derivatives, protein hydrolysate, amino acids, preservatives, chelating agents, stabilizers, antioxidants, plant extracts, crude drug extracts, vitamins, fragrance, and ultraviolet ray absorbers.

[pH]

The pH (25° C.) of the two-part hair dye of the present invention is preferably 8 to 12, more preferably 9 to 11, and even more preferably 9 to 10 upon application (at the time of mixing) in view of bleaching and hair dyeing effects and skin irritation. Examples of a pH adjuster include, besides the aforementioned alkali agent, an inorganic acid such as hydrochloric acid and phosphoric acid; an organic acid such as citric acid, glycolic acid, and lactic acid; and a phosphoric acid salt such as monopotassium dihydrogen phosphate and disodium monohydrogen phosphate.

[Viscosity]

The viscosity of a liquid mixture of the first part and the second part is 1 to 300 mPa·s, preferably 5 to 200 mPa·s, more preferably 10 to 100 mPa·s. Herein, the measurement of viscosity is taken at a revolution speed of 60 rpm, 30 rpm, or 12 rpm for a subject of measurement having a viscosity of no more than 100 mPa·s, 100 to 200 mPa·s, or no less than 200 mPa·s, respectively, at 25° C. by a B-type rotational viscometer with rotor No. 1. Measurements are taken in the order of high revolution to low revolution, and the measurement is completed at the point when the measurement is taken without the indicator swinging past the maximum point. No further measurements are subsequently taken at lower revolutions.

As the viscosity of a liquid mixture of the first part and the second part is adjusted to be in the aforementioned range, easily-applicable foam volume can be realized and dripping of the liquid mixture applied to the hair can be prevented, while squeezing to discharge a foam from a squeeze foamer and the like becomes easy. In order to adjust the viscosity of the liquid mixture to the aforementioned range, a water-soluble solvent such as ethanol may be added, or the content and the kind of the surfactant, the polyols, the higher alcohol, and the like may be appropriately adjusted.

[Gas-Liquid Mixing Ratio]

The gas-liquid mixing ratio of air and the liquid mixture achieved by the foam discharge means of the foamer container is preferably 7 to 40 mL/g, more preferably 15 to 30 mL/g, in view of easy blending of the preparation into the hair and easy application. The gas-liquid mixing ratio referred to herein is a value measured as follows.

Firstly, the weight and the volume of a foam discharged at 25° C. are measured to obtain a gas-liquid mixing ratio. Into a squeeze foamer (Daiwa Can Company, a volume of 210 mL, the coarseness (aperture) of a mesh in a mixing chamber is 150 mesh (150 openings per inch (25.4 mm)), and that of a mesh closest to the discharge outlet is 200 mesh), 100 g of the liquid mixture is placed. Once the amount of remaining foam has reached 80 g, 20 g of foam is discharged into a 1000 mL graduated cylinder, and the volume of foam thus discharged is measured one minute after initiation of discharging. The volume of discharged foam thus obtained (mL) is divided by a weight of 20 g to give a gas-liquid mixing ratio (mL/g).

[Foamer Container]

In the present invention, a foamer container is a non-aerosol type container, which is used to discharge a liquid mixture of the first part and the second part in the form of a foam by mixing it with air without using a propellant. A preventive effect on spattering of discharged preparation can also be attained with use of a foamer container. Particularly, a non-aerosol type container can be produced at a lower cost than an aerosol type container, and it can be handled more safely during distribution as no high-pressure gas propellant needs to be used.

As the foamer container, a publicly-known pump foamer container with foam discharge means, a squeeze foamer container, an electric foamer, an accumulator pump foamer container, and the like can be used. Specific examples thereof include pump foamer E3 type, pump foamer F2 type (the products of Daiwa Can Company), a squeeze foamer (Daiwa Can Company), an electric foamer (Matsushita Electric Works, Ltd.), and an air spray foamer (Airspray International, Inc.) described in FOOD & PACKAGING (vol. 35, No. 10, pages 588 to 593 (1994); vol. 35, No. 11, pages 624 to 627 (1994); vol. 36, No. 3, pages 154 to 158 (1995)). As the foamer container to be used for the two-part hair dye of the present invention, a pump foamer container and a squeeze foamer container are preferable as they are inexpensive and can be handled easily.

A pump foamer container or a squeeze foamer container has a foam-forming unit such as a net. It preferably has a thin net so that, in a case that a liquid mixture of the first part and the second part is dried and solidified to cause clogging, the flow of foam generated by the next discharging immediately dissolves the solidified mass to resolve the clogging. In this case, the mesh of the net is preferably 50 to 280 mesh, more preferably 90 to 250 mesh, and even more preferably 130 to 220 mesh. Here, a mesh refers to the number of apertures per inch. Use of the net of the mesh within the above range enables formation of a creamy foam. Also, preferred examples of the material of the mesh include nylon and polyester.

In the foamer container used in the two-part hair dye of the present invention, it is preferable to set at least one sheet, preferably more than one sheets of such a net. Particularly, in view of economic efficiency, foam stability, and the like, it is preferable to set two sheets of such a net.

The part of the foamer container which is in contact with the content (the inner wall of the container, the inner wall of the foam discharge means, and the like) is preferably composed of a material resistant to corrosion by alkali and hydrogen peroxide while allowing permeation of oxygen generated by decomposition of hydrogen peroxide.

As the product form of the two-part hair dye of the present invention composed of the first part, the second part, and the foamer container, the first part and the second part may each be contained in containers separate from the foamer container, and they may be transferred to the foamer container and mixed upon application. Alternatively, one of the preparations is contained in the foamer container while the other is contained in a separate container, and the preparation in the separate container may be transferred to the foamer container upon application. In this case, the second part is contained in a gas-permeable container, especially a foamer container composed of an oxygen-permeable material (for example, polyethylene) for prevention of an increase in the pressure inside the container due to oxygen generated by decomposition of hydrogen peroxide. Meanwhile, a container though which oxygen hardly permeates needs to be used for the first part for prevention of oxidation of the oxidation dye.

[Application Method]

In order to dye or bleach the hair (particularly, the hair of the head) with the two-part hair dye of the present invention, the hair is preferably combed in advance. Because the hair becomes less likely to get tangled by combing during the re-foaming treatment to be described below, there is no fear of splattering of the liquid mixture. Further, after combing the hair, blocking needs not to be performed, which is usually performed in application of a hair dye composition. Furthermore, blocking is preferably not performed. Absence of blocking makes the below-described operation of application of a hair dye composition to the hair and re-foaming operation easy. Subsequently, the first part and the second part of the two-part hair dye of the present invention are mixed in the foamer container. The preparation discharged in the form of a foam from the container may be applied to the hair directly or using a tool such as hands or a brush. From the viewpoint of prevention of splattering and dripping of the preparation, the preparation is preferably discharged in (gloved) hands first, and then applied to the hair.

After application, the hair dye product is left on the hair for approximately 3 to 60 minutes, preferably approximately 5 to 45 minutes. At this time, from the viewpoints of ensuring prevention of dripping while the hair dye product is left on the hair and adequately covering also the hair root with the liquid mixture, the hair dye product is preferably re-foamed on the hair. For re-foaming, gas may be infused, a tool such as a vibrating device and a brush or fingers may be used, and fingers are more preferably used.

At this point, re-foaming may be performed after complete disappearance of the foam, during disappearance of the foam, or before the foam applied undergoes changes. Alternatively, re-foaming may be performed after completion of application of the foam to the entire range of areas to which the hair dye product is intended to be applied or during application. Re-foaming may be performed continuously once or intermittently repeated multiple times.

After these operations, the liquid mixture is rinsed off. Subsequently, the hair is appropriately shampooed and conditioned, and then rinsed with water, followed by drying.

EXAMPLES

Examples 1 to 8, Comparative Examples 1 to 5

The first part and the second part having compositions as shown in Tables 1 and 2 (mass %) were prepared, which were mixed at a ratio of 1:1.5 to prepare a liquid mixture. Four tresses of Chinese white hair manufactured by Beaulax Co., Ltd., each weighing 1 g and being 10 cm in length, were prepared for each Example and Comparative Example.

The liquid mixture of 30° C. was discharged in the form of a foam from a squeeze foamer (S1 squeeze foamer manufactured by Daiwa Can Company, a volume of 210 mL, the coarseness of a mesh in a mixing chamber is 150 mesh and that of a mesh closest to the discharge outlet is 200 mesh, the total area of the narrowest opening of an air induction passage is 0.27 mm$^2$, and the inner diameter of a dip tube is 1.7 mm).

The foam of the liquid mixture was applied to the hair in a ratio of 1 to 1, and then left for 30 minutes. Subsequently, the four tresses were immersed in 100 mL of ion exchange water all together, and left for one minute. Then, the tresses were shampooed using a shampoo shown below and dried, which served as evaluation samples of pre-shampooed hair.

The value of color difference $\Delta E_0$ from before hair dyeing was measured in the evaluation samples thus obtained with a colorimeter CR-400 manufactured by Konica Minolta Sensing, Inc. Two tresses with median $\Delta E_0$ values were used in the following tests. The evaluation samples were each tress placed in a test tube NS-10 manufactured by As One Corporation. The tubes were adequately filled with a 10-fold diluted solution of the shampoo shown below and sealed. Subsequently, the samples were treated at 40° C. and a shaking speed of 120 rpm using a water bath shaker MM-10 manufactured by TAITEC Corporation for 30 minutes. After treatment, the tresses were rinsed with water and dried, which served as evaluation samples of shampooed hair. The value of color difference $\Delta E_1$ from before hair dyeing was measured also in the evaluation samples of shampooed hair with the aforementioned colorimeter. Fastness to shampooing was evaluated according to the following evaluation criteria.

(Evaluation Method)

Comparing the difference between $\Delta E_0$ before shampooing and $\Delta E_1$ after shampooing ($\Delta E_0 - \Delta E_1$) with that of Comparative Example 4 (standard; ($\Delta E_0 - \Delta E_1 = 4.5$)), the following evaluation was made:

a: smaller by 1 or greater
b: smaller by 0.5 to 1
c: equivalent (within ±0.5)
d: larger by 0.5 or greater (Shampoo Used for Evaluation)

| | |
|---|---|
| Sodium POE (3) lauryl ether sulfate | 15.5 mass % |
| Lauric acid diethanolamide | 1.5 mass % |
| Tetrasodium edetate | 0.3 mass % |
| Sodium benzoate | 1.43 mass % |
| Ion exchange water | Balance |

(Foaming Properties at Low Temperature)

The first part and the second part having compositions as shown in Tables 1 and 2 were each sealed in containers and left in a constant temperature room at 5° C. for 24 hours. Subsequently, immediately after transferring these preparations to a room at 20° C., the first part and the second part were mixed at a mixing ratio (mass ratio) of 1:1.5 in the aforementioned squeeze foamer. The liquid mixture was then discharged in the form of a foam and observed for its foaming properties.

a: extremely uniform and fine foam
b: uniform and fine foam
c: ununiform and coarse foam
d: watery and cannot form a foam (Storage Stability)

The first part and the second part having compositions as shown in Tables 1 and 2 were each sealed in containers and left in a constant temperature room at −5° C. for one month. Subsequently, the preparations were visually evaluated according to the following criteria.

a: no change was observed
b: slight turbidity was observed
c: white turbidity was observed
d: precipitation formed

TABLE 1

| | | | Example | | | | | | | |
|---|---|---|---|---|---|---|---|---|---|---|
| (mass %; the content entirely represents the active amount) | | | 1 | 2 | 3 | 4 | 5 | 6 | 7 | 8 |
| First part | | toluene-2,5-diamine | 0.50 | 0.50 | 0.50 | 0.50 | 0.50 | 0.50 | 0.50 | 0.50 |
| | | resorcinol | 0.40 | 0.40 | 0.40 | 0.40 | 0.40 | 0.40 | 0.40 | 0.40 |
| | | meta-aminophenol | 0.10 | 0.10 | 0.10 | 0.10 | 0.10 | 0.10 | 0.10 | 0.10 |
| | (B) | sodium polyoxyethylene (5) lauryl ether acetate | — | — | — | — | — | 8.46 | 2.82 | 1.18 |
| | (B) | sodium cocoylglutamate | 9.60 | 7.20 | 7.20 | 7.20 | 2.40 | — | — | 6.00 |
| | (B)' | sodium polyoxyethylene lauryl ether sulfate (2.0 E.O.) | — | — | — | — | — | — | — | — |
| | | alkyl (8 to 16) glucoside | 2.00 | 2.00 | 2.00 | 2.00 | 2.00 | 2.00 | 2.00 | 2.00 |
| | | polyoxyethylene lauryl ether (23 E.O.) | 2.00 | 2.00 | 2.00 | 2.00 | 2.00 | 2.00 | 2.00 | 2.00 |
| | | polyoxyethylene(9) tridecyl ether | 0.50 | 0.50 | 0.50 | 0.50 | 0.50 | 0.50 | 0.50 | 0.50 |
| | | propylene glycol | 4.00 | 4.00 | 4.00 | 4.00 | 4.00 | 4.00 | 4.00 | 4.00 |
| | | ethanol | 9.50 | 9.50 | 9.50 | 9.50 | 9.50 | 9.50 | 9.50 | 9.50 |
| | (A) | dimethyldiallylammonium chloride-acrylic acid copolymer (*1) | 3.20 | 2.40 | 1.20 | 0.40 | 0.40 | 1.20 | 0.40 | 1.20 |
| | (A)' | dimethyldiallylammonium chloride-acrylic acid copolymer (*2) | — | — | — | — | — | — | — | — |
| | (A)' | dimethyldiallylammonium chloride-acrylamide copolymer (*3) | — | — | — | — | — | — | — | — |
| | | ammonia | 1.68 | 1.68 | 1.68 | 1.68 | 1.68 | 1.68 | 1.68 | 1.68 |
| | | ammonium bicarbonate | 8.00 | 8.00 | 8.00 | 8.00 | 8.00 | 8.00 | 8.00 | 8.00 |
| | | monoethanolamine | 2.40 | 2.40 | 2.40 | 2.40 | 2.40 | 2.40 | 2.40 | 2.40 |
| | | ascorbic acid | q.s. | q.s. | q.s. | q.s. | q.s. | q.s. | q.s. | q.s. |
| | | anhydrous sodium sulfite | q.s. | q.s. | q.s. | q.s. | q.s. | q.s. | q.s. | q.s. |
| | | tetrasodium edetate dihydrate | q.s. | q.s. | q.s. | q.s. | q.s. | q.s. | q.s. | q.s. |
| | | purified water in an amount that brings the total amount of the first part to 100 | balance | balance | balance | balance | balance | balance | balance | balance |
| Second part | | stearyltrimethylammonium chloride | 0.70 | 0.70 | 0.70 | 0.70 | 0.70 | 0.70 | 0.70 | 0.70 |
| | | polyoxyethylene (40) cetyl ether | 0.46 | 0.46 | 0.46 | 0.46 | 0.46 | 0.46 | 0.46 | 0.46 |
| | | cetanol | 0.74 | 0.74 | 0.74 | 0.74 | 0.74 | 0.74 | 0.74 | 0.74 |
| | | myristyl alcohol | 0.21 | 0.21 | 0.21 | 0.21 | 0.21 | 0.21 | 0.21 | 0.21 |
| | | hydroxyethanediphosphonic acid | 0.04 | 0.04 | 0.04 | 0.04 | 0.04 | 0.04 | 0.04 | 0.04 |
| | | oxyquinoline sulfate (2) | 0.04 | 0.04 | 0.04 | 0.04 | 0.04 | 0.04 | 0.04 | 0.04 |
| | | sodium hydroxide or phosphoric acid | *4 | *4 | *4 | *4 | *4 | *4 | *4 | *4 |
| | | hydrogen peroxide | 5.70 | 5.70 | 5.70 | 5.70 | 5.70 | 5.70 | 5.70 | 5.70 |

TABLE 1-continued

| (mass %; the content entirely represents the active amount) | Example 1 | Example 2 | Example 3 | Example 4 | Example 5 | Example 6 | Example 7 | Example 8 |
|---|---|---|---|---|---|---|---|---|
| purified water in an amount that brings the total amount of the second part to 100 | balance | balance | balance | balance | balance | balance | balance | balance |
| anion/cation equivalent ratio of Component(B)/Component(A) | 1.24 | 1.24 | 2.49 | 7.46 | 2.49 | 2.50 | 2.50 | 2.42 |
| viscosity of the liquid mixture (25° C., mPa·s) | 22 | 17 | 15 | 15 | 11 | 17 | 12 | 16 |
| evaluation fastness to shampooing based on Comparative Example 4 (a number in parenthesis represents $\Delta E_0 - \Delta E_1$ of each Example) | a (3.0) | a (2.9) | a (3.4) | a (3.0) | a (2.9) | a (3.4) | a (2.4) | a (3.1) |
| foaming properties at low temperature | a | a | a | a | a | a | a | a |
| storage stability | a | a | a | a | a | a | a | a |

TABLE 2

| (mass %; the content entirely represents the active amount) | | | Comparative Example 1 | 2 | 3 | 4 | 5 |
|---|---|---|---|---|---|---|---|
| First part | | toluene-2,5-diamine | 0.50 | 0.50 | 0.50 | 0.50 | 0.50 |
| | | resorcinol | 0.40 | 0.40 | 0.40 | 0.40 | 0.40 |
| | | meta-aminophenol | 0.10 | 0.10 | 0.10 | 0.10 | 0.10 |
| | (B) | sodium polyoxyethylene (5) lauryl ether acetate | — | — | 8.46 | 1.18 | 1.18 |
| | (B) | sodium cocoylglutamate | 7.20 | 7.20 | — | 6.00 | 6.00 |
| | (B)' | sodium polyoxyethylene lauryl ether sulfate (2.0 E.O.) | — | — | — | — | — |
| | | alkyl (8 to 16) glucoside | 2.00 | 2.00 | 2.00 | 2.00 | 2.00 |
| | | polyoxyethylene lauryl ether(23 E.O.) | 2.00 | 2.00 | 2.00 | 2.00 | 2.00 |
| | | Polyoxyethylene (9) tridecyl ether | 0.50 | 0.50 | 0.50 | 0.50 | 0.50 |
| | | propylene glycol | 4.00 | 4.00 | 4.00 | 4.00 | 4.00 |
| | | ethanol | 9.50 | 9.50 | 9.50 | 9.50 | 9.50 |
| | (A) | dimethyldiallylammonium chloride-acrylic acid copolymer (*1) | — | 3.20 | — | — | — |
| | (A)' | dimethyldiallylammonium chloride-acrylic acid copolymer (*2) | — | — | — | — | 1.20 |
| | (A)' | dimethyldiallylammonium chloride-acrylamide copolymer (*3) | — | — | — | — | — |
| | | ammonia | 1.68 | 1.68 | 1.68 | 1.68 | 1.68 |
| | | ammonium bicarbonate | 8.00 | 8.00 | 8.00 | 8.00 | 8.00 |
| | | monoethanolamine | 2.40 | 2.40 | 2.40 | 2.40 | 2.40 |
| | | ascorbic acid | q.s. | q.s. | q.s. | q.s. | q.s. |
| | | anhydrous sodium sulfite | q.s. | q.s. | q.s. | q.s. | q.s. |
| | | tetrasodium edetate dihydrate | q.s. | q.s. | q.s. | q.s. | q.s. |
| | | purified water in an amount that brings the total amount of the first part to 100 | balance | balance | balance | balance | balance |
| Second part | | stearyltrimethylammonium chloride | 0.70 | 0.70 | 0.70 | 0.70 | 0.70 |
| | | polyoxyethylene (40) cetyl ether | 0.46 | 0.46 | 0.46 | 0.46 | 0.46 |
| | | cetanol | 0.74 | 0.74 | 0.74 | 0.74 | 0.74 |
| | | myristyl alcohol | 0.21 | 0.21 | 0.21 | 0.21 | 0.21 |
| | | hydroxyethanediphosphonic acid | 0.04 | 0.04 | 0.04 | 0.04 | 0.04 |
| | | oxyquinoline sulfate (2) | 0.04 | 0.04 | 0.04 | 0.04 | 0.04 |
| | | sodium hydroxide or phosphoric acid | *4 | *4 | *4 | *4 | *4 |
| | | hydrogen peroxide | 5.70 | 5.70 | 5.70 | 5.70 | 5.70 |
| | | purified water in an amount that brings the total amount of the second part to 100 | balance | balance | balance | balance | balance |
| anion/cation equivalent ratio of (B)/(A), (B)/(A)', or (B)'/(A) | | | — | 0.93 | — | — | 2.96 |
| viscosity of the liquid mixture (25° C., mPa·s) | | | 10 | *5 | 10 | 10 | 12 |
| evaluation | | fastness to shampooing based on Comparative Example 4 (a number in parenthesis represents $\Delta E_0 - \Delta E_1$ of each Comparative Example) | c (4.0) | *5 | c (4.0) | standard (4.5) | c (4.3) |
| | | foaming properties at low temperature | a | *5 | a | a | a |
| | | storage stability | a | a | a | a | a |

(*1): Merquat 295, the product of Nalco Company; the mole fraction of cationic monomers was 95%.
(*2): Merquat 280, the product of Nalco Company; the mole fraction of cationic monomers was 65%.
(*3): Merquat 550, the product of Nalco Company; the mole fraction of cationic monomers was 30%.
*4: An amount that brings the pH of the second part to 3.6.
*5: Unmeasurable due to separation

What we claim is:

1. A two-part hair dye comprising a first part containing an alkali agent, a second part containing hydrogen peroxide, and a non-aerosol foamer container for discharging a liquid mixture of the first part and the second part in the form of a foam, wherein the liquid mixture comprises the following components (A) and (B):
   (A) a polymer or copolymer containing 70% or more mole fraction of diallyldimethyl quaternary ammonium salt monomer, and
   (B) an N-acylamino acid salt, an N-acyl-N-alkylamino acid salt, or an ether carboxylic acid salt,
   wherein, an equivalent ratio of an anion site of the component (B) to a cation site of the component (A) (anion/cation) is more than 1.

2. The two-part hair dye according to claim 1, wherein the Component (A) is a copolymer of a diallyldimethyl quaternary ammonium salt monomer and an acrylic acid or acrylamide monomer.

3. The two-part hair dye according to claim 1, wherein the content of the Component (A) in the liquid mixture is 0.1 to 1.5 mass %.

4. The two-part hair dye according to claim 1, wherein the content of the Component (B) in the liquid mixture is 0.5 to 5 mass %.

5. The two-part hair dye according to claim 1, further comprising an anionic surfactant other than the Component (B) or a cationic surfactant in an amount of 0 to 1 mass % in the liquid mixture.

6. The two-part hair dye according to claim 1, further comprising an amphoteric surfactant or a nonionic surfactant in an amount of 0.1 to 5 mass % in the liquid mixture.

7. The two-part hair dye according to claim 1, further comprising an oil agent in an amount of 0.01 to 3 mass % in the liquid mixture.

8. The two-part hair dye according to claim 1, wherein a pH of the liquid mixture at 25° C. is 8 to 12.

9. A method for dyeing hair comprising discharging the liquid mixture of the two-part hair dye according to claim 1 from a non-aerosol type foamer container in the form of a foam, applying the liquid mixture in the form of a foam thus discharged to the hair, and then re-foaming the liquid mixture on the hair.

10. The two-part hair dye according to claim 1, wherein (A) is a polymer or copolymer containing 80% or more mole fraction of diallyldimethyl quaternary ammonium salt monomer.

11. The two-part hair dye according to claim 1, wherein (A) is a polymer or copolymer containing 90% or more mole fraction of diallyldimethyl quaternary ammonium salt monomer.

12. The two-part hair dye according to claim 1, wherein (B) is an N-acylamino acid salt and said N-acylamino acid salt is at least one selected from the group consisting of N-lauroyl glutamate, N-myristoyl glutamate, N-stearoyl glutamate, N-cocoyl glutamate, and N-hydrogenated tallow glutamate.

13. The two-part hair dye according to claim 1, wherein (B) is an N-acyl-N-alkylamino acid salt and said N-acyl-N-alkylamino acid salt is at least one selected from the group consisting of an N-lauroyl-N-isopropyl glycine salt, an N-lauroyl sarcosine salt, an N-myristoyl sarcosine salt, an N-palmitoyl sarcosine salt, and an N-lauroyl-N-methyl-β-alanine salt.

14. The two-part hair dye according to claim 1, wherein (B) is an ether carboxylic acid salt and said ether carboxylic acid salt is at least one selected from the group consisting of a polyglyceryl alkyl ether acetic acid salt or an ether acetic acid salt.

15. The two-part hair dye according to claim 1, wherein (B) is an ether carboxylic acid salt and said ether carboxylic acid salt is at least one selected from the group consisting of a polyglyceryl alkyl ether acetic acid salt or an ether acetic acid salt represented by formula (1):

$$R-Z-(CH_2CH_2O)_m-CH_2CO_2X \quad (1)$$

wherein,
R is a linear or branched alkyl group or alkenyl group having a carbon number of 7 to 19,
Z is —O— or —CONH—,
X is a hydrogen atom, an alkali metal, triethanolamine, or ammonium, and
m is a number ranging from 1 to 20.

16. The two-part hair dye according to claim 5, wherein said two-part hair dye comprises an anionic surfactant other than the Component (B) and said anionic surfactant other than the Component (B) is at least one selected from the group consisting of alkyl sulfate and alkyl ether sulfate.

17. The two-part hair dye according to claim 5, wherein said two-part hair dye comprises a cationic surfactant and said cationic surfactant is a mono long-chain alkyl quaternary ammonium salt.

18. The two-part hair dye according to claim 6, wherein said two-part hair dye comprises an amphoteric surfactant and said amphoteric surfactant is at least one selected from the group consisting of carbobetaine, amidobetaine, sulfobetaine, hydroxyl sulfobetaine, amidosulfobetaine, phosphobetaine, and a imidazolinium surfactant having an alkyl group, an alkenyl group, or an acyl group with a carbon number of 8 to 24.

19. The two-part hair dye according to claim 6, wherein said two-part hair dye comprises a nonionic surfactant and said nonionic surfactant is at least one selected from the group consisting of an alkyl polyglucoside, a polyoxyalkylene alkyl ether, and an alkyl glyceryl ether.

20. The two-part hair dye according to claim 1, wherein the equivalent ratio of an anion site of the component (B) to a cation site of the component (A) (anion/cation) is 1.1 to 20.

* * * * *